(12) United States Patent
Chamney et al.

(10) Patent No.: US 10,737,009 B2
(45) Date of Patent: *Aug. 11, 2020

(54) METHOD FOR ASSESSING A PATIENT'S FLUID STATUS AND/OR SENSITIVITY TO FLUID REMOVAL, CONTROLLER, AND DEVICES

(71) Applicant: FRESENIUS MEDICAL CARE DEUTSCHLAND GMBH, Bad Homburg (DE)

(72) Inventors: Paul Chamney, Herts (DE); Ulrich Moissl, Karben (DE); Peter Wabel, Darmstadt (DE); Volker Nier, Reichelsheim (DE); Sebastian Wieskotten, Ober-Ramstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 284 days.

This patent is subject to a terminal disclaimer.

(21) Appl. No.: 15/179,499

(22) Filed: Jun. 10, 2016

(65) Prior Publication Data

US 2016/0361480 A1 Dec. 15, 2016

Related U.S. Application Data

(63) Continuation of application No. 14/461,902, filed on Aug. 18, 2014, now Pat. No. 9,486,567, which is a (Continued)

(30) Foreign Application Priority Data

Oct. 22, 2009 (EP) ..................................... 09013356

(51) Int. Cl.
*A61M 1/16* (2006.01)
*A61B 5/03* (2006.01)
(Continued)

(52) U.S. Cl.
CPC ........... *A61M 1/1603* (2014.02); *A61B 5/026* (2013.01); *A61B 5/03* (2013.01); *A61B 5/1455* (2013.01);
(Continued)

(58) Field of Classification Search
CPC .. A61M 1/14; A61M 1/1601; A61M 2205/33; A61M 2205/3303;
(Continued)

(56) References Cited

U.S. PATENT DOCUMENTS 5,280,429 A 1/1994 Withers
6,061,590 A 5/2000 Krivitski
(Continued)

FOREIGN PATENT DOCUMENTS

CN 101291617 10/2008
EP 1872811 1/2008
(Continued)

OTHER PUBLICATIONS

Ishibe, 2004, "Methods of Assessment of Volume Status and Intercompartmental Fluid Shifts in Hemodialysis Patients: Implications in Clinical Practice," Seminars in Dialysis, Waverly Press, Baldimore, MD, vol. 17, No. 1, pp. 37-43. [cited in parent].
(Continued)

*Primary Examiner* — Leslie R Deak
(74) *Attorney, Agent, or Firm* — Fish & Richardson P.C.

(57) ABSTRACT

The present invention relates to a method for assessing a patient's sensitivity to fluid removal from the patient's vascular system or to fluid replacement or addition with regard to the patient's hydration state, the method comprising the step of determining a value reflecting the distribution of fluid between at least two distribution spaces of the body of the patient or changes thereof from measured or calculated values, and assessing whether the value fulfills at least
(Continued)

one criterion. It also relates to a controller, an apparatus, a device, a digital storage device, a computer program product, and a computer program.

17 Claims, 9 Drawing Sheets

Related U.S. Application Data continuation of application No. 13/503,139, filed as application No. PCT/EP2010/006433 on Oct. 21, 2010, now Pat. No. 8,827,942.

(60) Provisional application No. 61/253,878, filed on Oct. 22, 2009.

(51) Int. Cl.
| | |
|---|---|
| *A61M 1/14* | (2006.01) |
| *A61M 1/36* | (2006.01) |
| *A61B 5/1455* | (2006.01) |
| *A61B 5/026* | (2006.01) |
| *A61M 1/34* | (2006.01) |
| *G05B 15/02* | (2006.01) |
| *A61B 5/027* | (2006.01) |

(52) U.S. Cl.
CPC ............ *A61M 1/14* (2013.01); *A61M 1/1601* (2014.02); *A61M 1/3403* (2014.02); *A61M 1/3607* (2014.02); *A61M 1/3609* (2014.02); *G05B 15/02* (2013.01); *A61B 5/027* (2013.01); *A61B 5/0261* (2013.01); *A61B 5/14557* (2013.01); *A61M 2205/058* (2013.01); *A61M 2205/33* (2013.01); *A61M 2205/3303* (2013.01); *A61M 2205/3306* (2013.01); *A61M 2205/3334* (2013.01); *A61M 2205/3344* (2013.01); *A61M 2205/50* (2013.01); *A61M 2205/502* (2013.01); *A61M 2205/52* (2013.01); *A61M 2230/005* (2013.01); *A61M 2230/20* (2013.01); *A61M 2230/201* (2013.01); *A61M 2230/207* (2013.01); *A61M 2230/65* (2013.01)

(58) Field of Classification Search
CPC .. A61M 2205/3306; A61M 2205/3334; A61M 2205/3344; A61M 2205/50; A61M 2205/52; A61M 2230/005; A61M 2230/20; A61M 2230/201; A61M 2230/207; A61M 2230/65; A61B 5/026

USPC .................. 604/4.01, 5.04, 5.01, 6.09, 6.11; 210/645, 739, 746; 702/19
See application file for complete search history.

(56) References Cited

U.S. PATENT DOCUMENTS

| | | | |
|---|---|---|---|
| 6,780,322 B1 | 8/2004 | Bissler et al. | |
| 8,827,942 B2 * | 9/2014 | Chamney | A61B 5/026 |
| | | | 604/6.09 |
| 9,486,567 B2 * | 11/2016 | Chamney | A61B 5/026 |
| 2004/0057037 A1 | 3/2004 | Ohishi et al. | |
| 2004/0064063 A1 | 4/2004 | Chamney | |
| 2005/0039763 A1 | 2/2005 | Kraemer et al. | |
| 2005/0102165 A1 | 5/2005 | Oshita et al. | |
| 2006/0226079 A1 | 10/2006 | Mori et al. | |
| 2007/0108129 A1 | 5/2007 | Mori et al. | |
| 2007/0273504 A1 | 11/2007 | Tran | |
| 2008/0013747 A1 | 1/2008 | Tran | |
| 2009/0182204 A1 | 7/2009 | Semler et al. | |

FOREIGN PATENT DOCUMENTS

| | | |
|---|---|---|
| JP | H06-506854 | 8/1994 |
| JP | 2001321352 | 11/2001 |
| JP | 2004-097781 | 4/2004 |
| JP | 2004-512128 | 4/2004 |
| JP | 2005-512665 | 5/2005 |
| JP | 2006-288625 | 10/2006 |
| JP | 2007-130300 | 5/2007 |
| WO | 02/053209 | 7/2002 |
| WO | 2004062235 | 7/2004 |

OTHER PUBLICATIONS

PCT International Search Report from PCT/EP2010/006433, dated Feb. 2, 2011. [cited in parent].
Piccoli, 2004, "Bioelectric impedance vector distribution in peritoneal dialysis patients with different hydration status," Kidney International, Nature Publishing Group, London, vol. 65, pp. 1060-1063. [cited in parent].
Wabel et al., 2009, "Importance of Whole-Body Impedance Spectroscopy for the Management of Fluid Balance," Blood Purification, vol. 27, pp. 75-80. [cited in parent].
Wizerman et al., 2009, "The mortality risk of overhydration in haemodialysis patients," Nephrology Dialysis Transplantation, Oxford University Press, Great Britain, pp. 1-6. [cited in parent].
Sakamoto et al., "Electrical admittance method for estimating fluid removal during artificial dialysis," Medical and Biological Engineering and Computing, May 2004, 42(3), pp. 356-365.
European Search Report in European Application No. 09013356, dated Mar. 10, 2010, 5 pages (with English translation).

\* cited by examiner

METHOD FOR ASSESSING A PATIENT'S FLUID STATUS AND/OR SENSITIVITY TO FLUID REMOVAL, CONTROLLER, AND DEVICES

CROSS-REFERENCE TO RELATED APPLICATIONS

This application is a continuation application of U.S. patent application Ser. No. 14/461,902, filed on Aug. 18, 2014, which is incorporated herein by reference in its entirety, and which is a continuation of U.S. patent application Ser. No. 13/503,139, filed on Apr. 20, 2012, which is a 371 national phase application of PCT/EP2010/006433 filed Oct. 21, 2010, which claims priority from European Application No. EP 09013356.2, filed on Oct. 22, 2009, and U.S. Provisional Patent Application No. 61/253,878, filed on Oct. 22, 2009.

FIELD OF INVENTION

The present invention relates to a method for assessing a patient's fluid status and/or sensitivity to fluid removal from the patient's vascular system—or to fluid replacement or fluid addition—with regard to the patient's hydration state, the method comprising the step of determining a value reflecting the distribution of a fluid between at least two distribution spaces of the body of the patient or changes thereof from measured or calculated values, and assessing whether the value fulfills at least one criterion. It also relates to a controller, an apparatus, a device, a digital storage means, a computer program product, and a computer program.

BACKGROUND OF THE INVENTION

Quite frequently, patients are treated with regard to their fluid balance. Likewise, such a treatment may be directed to the removal of fluid or to the replacement or addition of fluid. The present invention aims at providing a method and devices applicable in the field or context of fluid balance or fluid status.

By means of the present invention a method for assessing a patient's sensitivity to fluid removal from the patient's vascular system—or to fluid replacement or fluid addition—with regard to the patient's hydration state is suggested. Also, a controller for carrying out the method according to the present invention is provided, as well as an apparatus, a device comprising the present invention, a controller, a digital storage means, a computer program product, and a computer.

The method according to the present invention is defined by the feature combination of claim 1. Accordingly, in one aspect of the present invention, an assessment is suggested comprising the step of determining a value reflecting the distribution of a fluid between at least two distribution spaces (also referred to as a first and a second distribution space below) of the body of the patient, or reflecting changes of the value or reflecting changes of one or more of the distribution spaces. It further comprises assessing whether the value fulfills at least one criterion.

The patient can be either a human being or an animal. The patient may be sound or ill. The patient may be in need of medical care or not. The patient may be a dialysis patient or not.

In another aspect of the present invention, the controller is intended or provided or used or configured to carry out the method according to the present invention.

In yet another aspect of the present invention, an apparatus is provided, the apparatus comprising means for obtaining a value reflecting or concerning the distribution of a fluid between at least a first and a second distribution space of the patient, and at least one controller according to the present invention.

In another aspect of the present invention, the digital storage means, in particular a disc, CD or DVD, has electrically readable control signals which are able to interact with a programmable computer system such that the method according to the present invention will be executed.

In another aspect of the present invention, the computer program product has a program code stored on a machine readable data medium for executing the method according to the present invention when executing the program product on a computer.

In another aspect of the present invention, the computer program has a program code for the execution of a method according to the present invention when executing the program on a computer.

Embodiments can include one or more of the following features.

In certain embodiments, the value reflecting the distribution or changes thereof is determined from one or more measured or calculated values and/or figures and/or terms, the measured or calculated value(s), figure(s), and term(s) being different from the value to be determined.

In some embodiments, the measured or calculated values and/or figures and/or terms are gained in the presence of the patient.

In certain embodiments, the measured or calculated values and/or figures and/or terms are gained in the absence of the patient (that is, without the patient being present). For example, the measured or calculated values and/or figures and/or terms may be already at hand when carrying out the method according to the present invention. For example, in some embodiments, the measured or calculated values and/or figures and/or terms were collected in advance of carrying out the method according to the present invention.

In some embodiments, the fluid is a body fluid such as blood or water comprised within the body, e.g. extracellular water. In certain embodiments, the fluid is one fluid, in particular one body fluid.

In certain embodiments, the fluid is incorporated or is intended to be incorporated, e.g. as drinking water, as replacement fluid as it is known in the art, etc.

In some embodiments, the first or the second distribution space is defined as the blood volume.

In certain embodiments, the second distribution space is the extracellular fluid volume.

In some embodiments, the second distribution space are the interstices, the interstitium, or the interstitial volume, respectively.

In some embodiments, the method further includes determining a saturation degree of at least one of the distribution spaces and using said saturation degree as value or as criterion.

In certain embodiments, the saturation degree is determined by means of a curve. The saturation degree can be a numerical parameter, a "0/1" information, or any other type of information that indicates the saturation, e.g., the slope of a curve indicating the distribution of the fluid at issue between two or more distributions spaces, or what is defined or approximated as saturation by the skilled one.

In some embodiments, the saturation degree is a ratio between the sizes of two distribution spaces, or a ratio between changes of two distribution spaces over time, and the like.

In certain embodiments, the saturation degree indicates, what percentage or part of additional fluid will be incorporated by a first distribution space and what percentage or part will be incorporated by one or more distribution space different from the first distribution space.

In certain embodiments, the method further includes determining a saturation degree based on the Guyton curve—with the Guyton curve being a curve depicting the blood volume BV over the extracellular fluid volume ECW of a patient explaining physiologic interdependencies between extracorporeal water (ECW) and the blood volume—or an adaption thereof to human beings or particulars.

In some embodiments, the method further includes calculating a correlation between changes in weight—particular pre-weight, i.e., a dialysis patient's weight at the beginning of another dialysis treatment, respectively—over at least two measurements and values representing an anemia state of the patient or changes thereof at those measurements. The patient can be a dialysis patient.

In certain embodiments, the anemia state of the patient is defined by means of direct or indirect measurements or calculations of the mass, the concentration or the volume of a substance, e.g. hemoglobin (Hb), or changes thereof.

In some embodiments, the anemia state of the patient is defined by means of direct or indirect measurements or calculations of the haematocrit (Hct) or changes thereof.

In certain embodiments, the method further includes comparing the calculated correlation with a threshold or a range.

In some embodiments, the threshold or range is predetermined or pre-set.

In certain embodiments, the threshold is the slope or inclination of a curve in a graphical illustration.

In some embodiments, the range is a combination of—more than one—thresholds.

In certain embodiments, the result of the assessment may be the finding that the value falls or does not fall within a range. For example, the result may be that the value is above or below a threshold.

In some embodiments, the method further includes assessing the size of at least one distribution space based on measured values and/or results of calculations reflecting a hemoglobin (Hb) state. The hemoglobin (Hb) state may be reflected by the Hb concentration, its total mass, its volume, change thereof over time, respectively, etc.

In certain embodiments, the method further includes assessing the size of at least one distribution space based on measured values and/or results of calculations reflecting the haematocrit (Hct) or changes thereof over time.

As is evident to the skilled person, the present invention is not limited to the assessment of the size of at least one distribution space based on measured values and/or results of calculations reflecting a hemoglobin (Hb) state or the haematocrit (Hct) or changes thereof. The present invention can of course also be carried out based on measured values and/or results of calculations reflecting a mass, concentration or volume (and changes thereof) of any other suitable substance or marker.

In some embodiments, the method further includes using the size of at least one distribution space as was obtained based on results from measurement of blood samples and/or from blood comprised in extracorporeal blood lines by means of an appropriate monitor. The measurements can be made—or were made or terminated before carrying out the method according to the present invention—by measuring the optical properties of the blood by optical sensors and/or by assessing acoustic properties like transit times and/or propagations velocities of ultrasonic pulses by ultrasonic sensors.

Also, in certain embodiments any samples used for measurements were obtained before carrying out the method according to the present invention.

For determining the hydration state also any appropriate monitor can be used, such as monitors based on bioimpedance or dilution techniques.

In certain embodiments, the method further includes using the size of at least one distribution space as obtained based on results from urine samples.

In some embodiments, the method further includes using the size of at least one distribution space as obtained based on results from tissue samples.

In certain embodiments, the method further includes using the size of at least one distribution space as obtained based on results obtained from measuring a concentration, mass, volume or changes thereof of a substance being comprised by the group comprising at least any substance produced naturally in the body of the patient, in particular hemoglobin, albumin, insulin, glucose, C-reactive protein (CRP), and non-endogeneous substances, in particular pharmaceutically effective substances.

In some embodiments, the method further includes assessing pre-dialysis values of the patient.

In certain embodiments, the pre-dialysis values represent the patient's condition(s) seconds or minutes (up to, e.g., a half-hour, one hour, two hours or the like) before starting the next dialysis treatment.

In some embodiments, the method further includes assessing post-dialysis values of the patient.

In certain embodiments, the post-dialysis values represent the patient's condition(s) seconds or minutes (up to, e.g., a half-hour, one hour, two hours or the like) after finishing the next dialysis treatment.

In certain embodiments, the method further includes plotting results of the assessment for visual assessment.

In some embodiments, the at least one criterion is, or comprises, at least one threshold or at least one range.

In certain embodiments, the at least one criterion is pre-set or predetermined.

In some embodiments, the at least one criterion is variable.

In certain embodiments, the method further includes determining the criterion.

In some embodiments, the method further includes the step of calculating and/or measuring parameters reflecting the volume of at least one of the distribution spaces of the patient or an approximation thereof.

In certain embodiments, the method further includes determining or adjusting a dosage of a medicament to be administered to a patient for improving the patient's anemia state based on the obtained relation between the calculated or measured value(s) and the criterion.

In some embodiments, the controller comprises means for obtaining information concerning the distribution or the distribution space(s). In certain embodiments, the means may be a monitor for obtaining information concerning the distribution, an input means for inputting information concerning the distribution or the distribution space(s), or the like.

In certain embodiments, the apparatus is or comprises a monitor for obtaining information concerning the distribution.

In some embodiments, the monitor for obtaining data related to the distribution and/or for obtaining data reflecting the relation between the sizes or the volumes of at least two distribution spaces is a monitor as described in WO 2006/002685 A1. The respective disclosure of WO 2006/002685 A1 is hereby incorporated in the present application by way of reference. Of course, the present invention must not be understood to be limited to monitors obtaining data by bioimpedance measurements as is described in WO 2006/002685 A1. Other bioimpedance methods known in the art and also any other methods known in the art such as dilution measurements and also any other method known to the skilled person are also contemplated and encompassed by the present invention as well.

In certain embodiments, the apparatus comprises a monitor for measuring Hb concentrations (e.g., in [g/dl]) and/or for determining the blood volume by means of any monitor as described in "*Replacement of Renal Function by Dialysis*" by Drukker, Parson and Maher, Kluwer Academic Publisher, 5$^{th}$ edition, 2004, Dordrecht, The Netherlands, on pages 397 to 401 ("*Hemodialysis Machines and Monitors*"), the respective disclosure of which is hereby incorporated by way of reference.

In some embodiments, the monitor is configured to measure the blood volume and/or the concentration of the substance—in particular Hb—by means of measuring an electrical conductivity.

In certain embodiments, the monitor is configured to measure the blood volume and/or the concentration of the substance—in particular Hb—by means of measuring an optical density.

In some embodiments, the monitor is configured to measure the blood volume and/or the concentration of the substance—in particular Hb—by means of measuring a viscosity.

In certain embodiments, the monitor is configured to measure the blood volume and/or the concentration of the substance—in particular Hb—by means of measuring a density.

In some embodiments, the monitor comprises one or more corresponding probes and/or one or more sensors for carrying out the measurements such as electrical conductivity sensors, optical sensors, viscosity sensors, density sensors, and the like.

In certain embodiments, the apparatus furthermore comprises an output device for outputting results provided by the controller.

In some embodiments, the output device is a monitor having a display, a plotter, a printer or any other means for providing an output.

In certain embodiments, the output device is connected to an actuator for controlling administration of a substance to the patient.

In certain embodiments, the device may be used for treating a patient by means of dialysis.

In other embodiments, the device may be used for treating a patient (or the patient's blood) by hemofiltration, ultrafiltration, hemodialysis, etc.

The embodiments may provide one or more of the following advantages.

In some embodiments, the present invention provides information on the question into what body compartment or distribution space a fluid, e.g. drinking water or a replacement fluid, goes to when ingested by the patient. In particular, by means of certain embodiments of the present invention, a distinction can be made whether ingested fluids increase, for example, the blood volume or the interstices or both. This distinction may help to understand the patient's sensitivity to fluid removal. It may contribute to a more thorough understanding of cardiovascular circumstances and conditions, in particular cardiovascular stress. In some embodiments, this distinction can be readily made on basis of the measured or calculated values reflecting increases of, for example, weight and Hb.

In certain embodiments, by means of the present invention it can be found out whether the administration of volume (i.e., a fluid) to the patient—e.g, by means of replacement solutions such as HAES® and the like—can be of advantage to the patient. This is particularly possible in cases where the concentration, or mass, or volume of a substance at issue—such as hemoglobin—is constant over time or can be approximated to be so.

In some embodiments, by means of the present invention it can be determined whether an on-going replacement of volume by means of solutions such as HAES® or addition of fluid is better stopped.

Further, dialysis patients with accumulated extravascular fluid—as it is the case with anasarca or edema—can also benefit from certain embodiments of the present invention: Fluid which increases the volume of such an accumulated extravascular fluid can be identified by means of the method according to the present invention. Consequently, such a patient will be correctly considered as overhydrated—even if, e.g., the patient's reaction during ultrafiltration indicates a dry state. Accordingly, the dialysis, e.g. the ultrafiltration rate or duration, may be adapted to the actual need of the patient. The same advantage may apply upon adoption or administration of diuretics which is also contemplated by the present invention. This advantage is not limited to dialysis patients.

Other aspects, features, and advantages will be apparent from the description, figures, and claims.

BRIEF DESCRIPTION OF THE DRAWINGS

In the following, the present invention is further explained by means of the figures of the drawing. However, the present invention must not be understood to be limited to the examples explained by means of the figures.

DETAILED DESCRIPTION OF THE DRAWINGS

Figure 1:
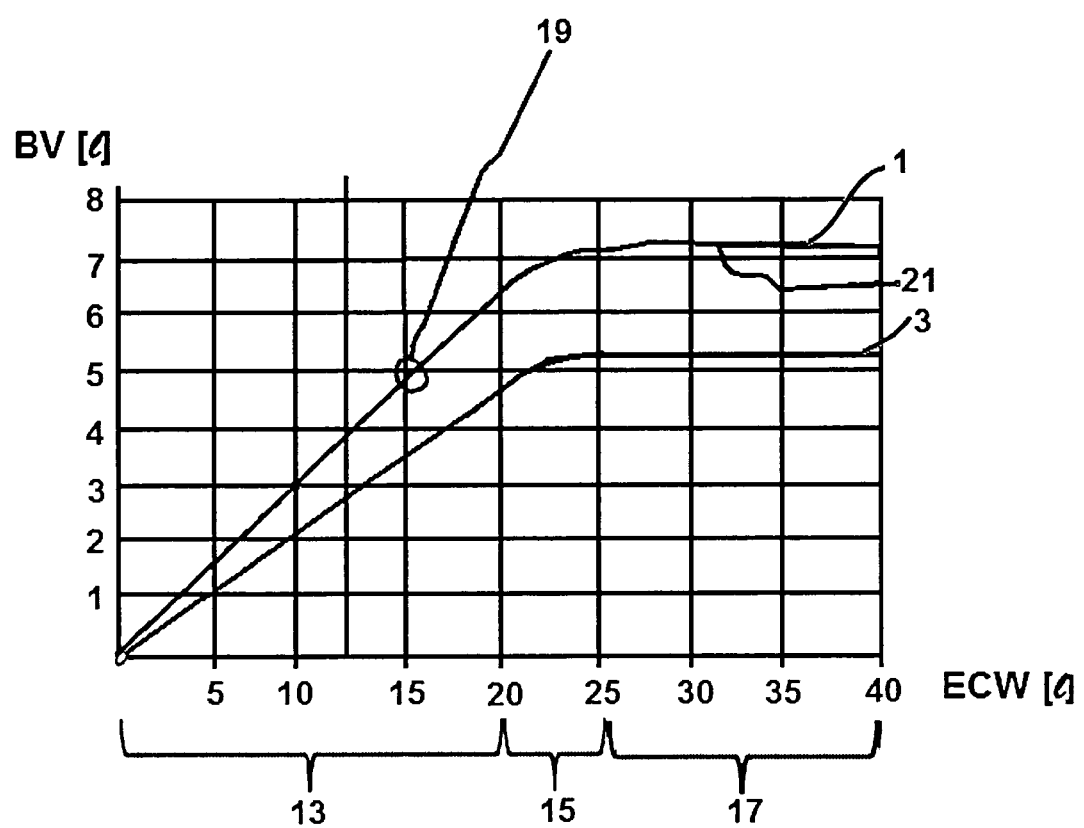
FIG. 1 shows two Guyton curves depicting the blood volume of two patients over their extracellular volume.

FIG. 1 shows a first Guyton curve 1 depicting the blood volume BV in litres over the extracellular fluid volume ECW in litres of a first patient and a second Guyton curve 3 of a second patient.

Curve 1 extends in a straight manner through a linear range 13 with a more or less constant first slope between 0 and about 20 litres of extracellular fluid volume ECW. Between 20 and 23 litres of extracellular fluid volume ECW the slope of curve 1 decreases in a transition region 15, and between 23 and 40 litres of extracellular fluid volume ECW the curve extends again in a more or less straight manner with a more or less constant second slope in a so-called saturation range 17.

The shape of curve 3 is similar to that of curve 1 but has a different slope and height.

Curve 1 runs through a "normal range" 19 that can be found both within the linear range 13 of curve 1. The normal range 19 represents a distribution of fluid between blood and extracellular fluid that is frequently found in healthy conditions. It shows a normal distribution of water comprised by the body between the blood volume and the extracellular fluid volume. In contrast, point 21 represents a misdistribution of fluid between blood and extracellular fluid. This misdistribution is frequently found by people being strongly overhydrated (be it for kidney or heart failure or other reasons).

Range 17 of the curve 1 can be understood as a saturation range indicating that additional volume (e.g., administered via indwelling catheter or ingested by drinking) would further increase the interstitial fluid volume, and only to a lesser degree the blood volume—if at all.

Figure 2:
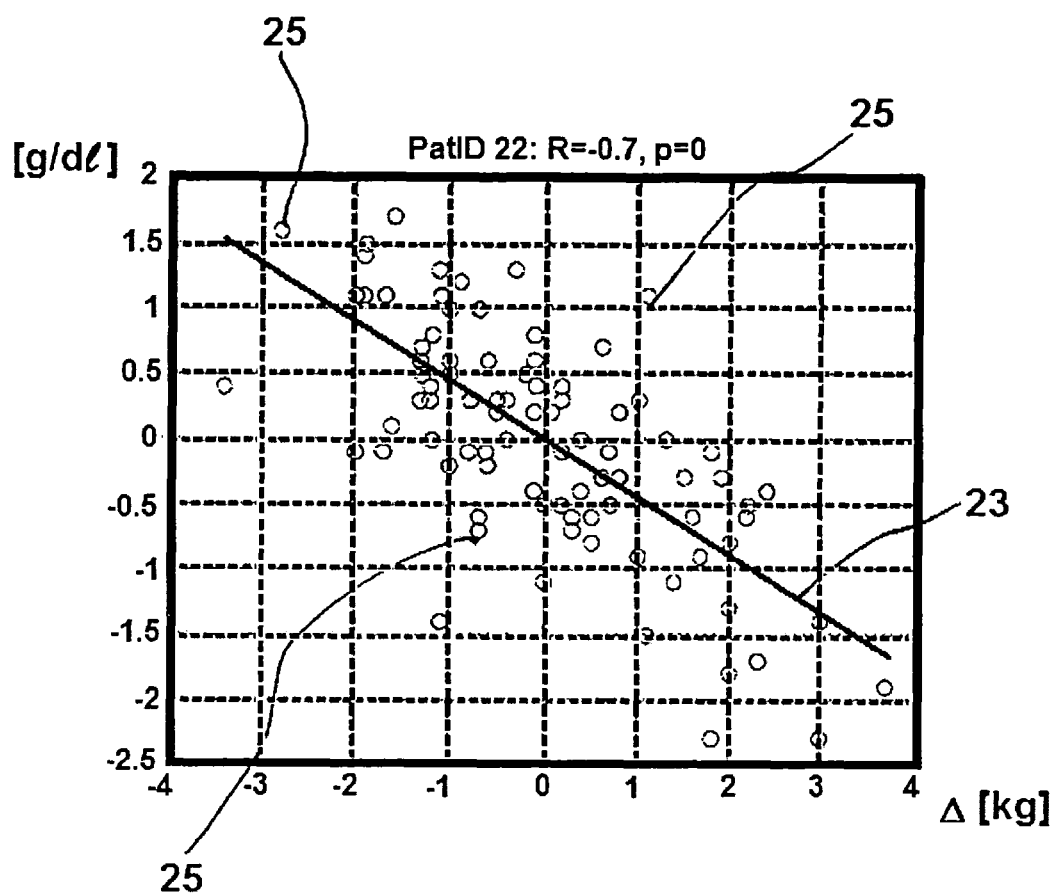
FIG. 2 shows a correlation between day-by-day changes in pre-weight in [kg] and day-by-day changes in hemoglobin (Hb) in [g/dl]

FIG. 2 shows a correlation between day-by-day changes in pre-weight (x-axis, in [litres]) and day-by-day changes in hemoglobin (y-axis, in [g/dl] Hb) of an anonymized patient "PatID 22"). The plot of FIG. 2 depicts the day-by-day (alternatively the treatment-by-treatment) change in Hb over the patient's change in pre-weight measured at the same occasions as the Hb concentration. For example, if a patient has a pre-weight of 70 kg on treatment day 1, and a pre-weight of 72 kg on treatment day 2, the patient's delta pre-weight is +2 kg. If the patient's Hb is 10 g/dl on treatment day 1 and 9 g/dl on treatment day 2, the patient's delta Hb is −1 g/dl. As the change in pre-weight is assumed to be caused by body water changes only—or mainly, and only secondarily by food, different clothing, etc.—amendments of a distribution space can be reflected, assumed or approximated this way.

As can be seen from a regression line 23 which is calculated based on values 25 reflecting the results of corresponding measurements in a known manner, higher pre-weights—compared to the preceding treatment—result in lower Hb concentrations. It is hence assumed that the weight reflects water intake, especially over short time periods in which a change in flesh weight is unlikely. Since a significant correlation can be seen in this patient, the patient obviously is not in the saturation range 17 of the Guyton curve shown in FIG. 1 with BV over extracellular water (ECW): an increase in blood volume (in line with increased pre-weight) results in a reduced Hb concentration. In other words, increased water intake (increased pre-weight) seems to dilute Hb (decreased concentration of hemoglobin in the blood compartment) under the assumption that Hb mass is constant.

Figure 3:
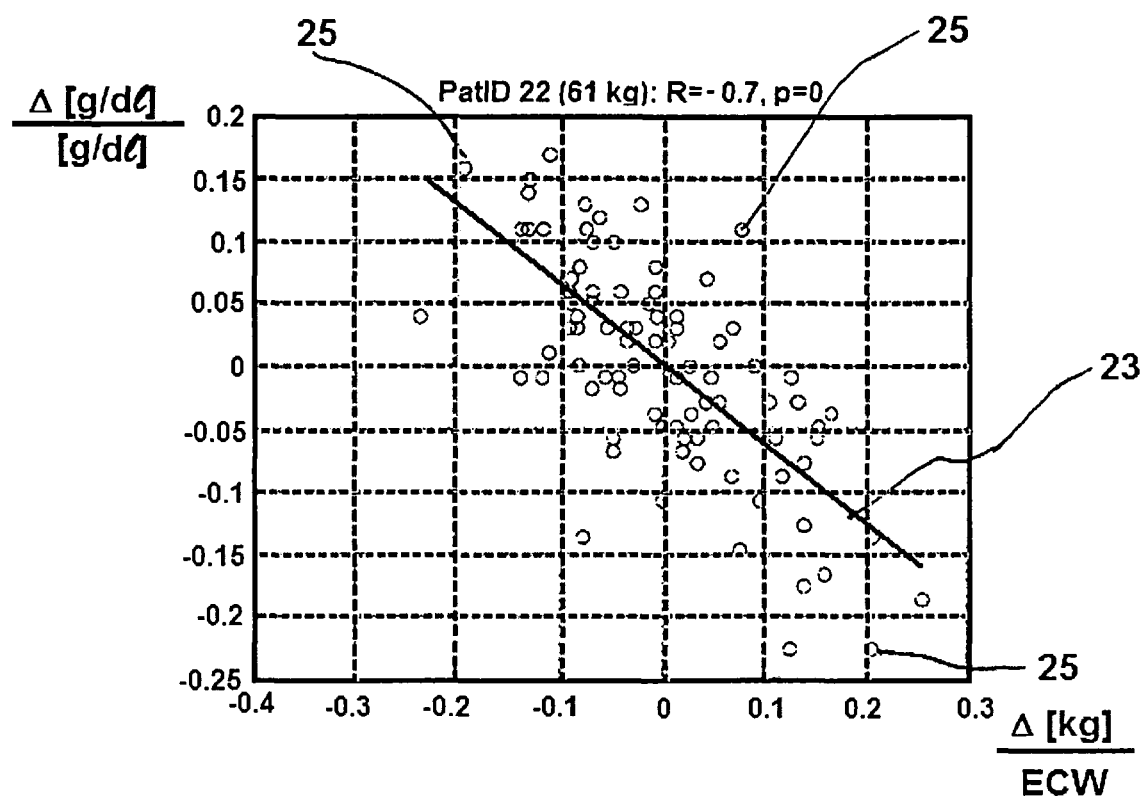
FIG. 3 shows the data of FIG. 2, illustrated in relative terms.

FIG. 3 shows the data of FIG. 2, illustrated in relative terms, depicted as delta Hb relative to/over the averaged or mean Hb (see y-axis), over delta pre-weight relative to/over extracellular water (ECW) (see x-axis). The slope of the regression line 23 reflects that a 10% increase in ECW results in a 6.3% increase in BV (equals a 6.3% decrease in Hb concentration, measured in the patient's blood).

For the linear range of the Guyton curve one would expect that a 10% increase in ECW corresponds to a 10% increase in BV (1:1 ratio, see range 13 of FIG. 1). Since the slope of the curve shown in FIG. 3 reveals one only a 6.3% for this patient, this may indicate that the patient is already close to saturation (that is, in or close to the range 17 of FIG. 1).

It is noted that the explanations given with respect to FIG. 3 (i.e., in the preceding two paragraphs) relate to the intake of liquid.

Figure 4:
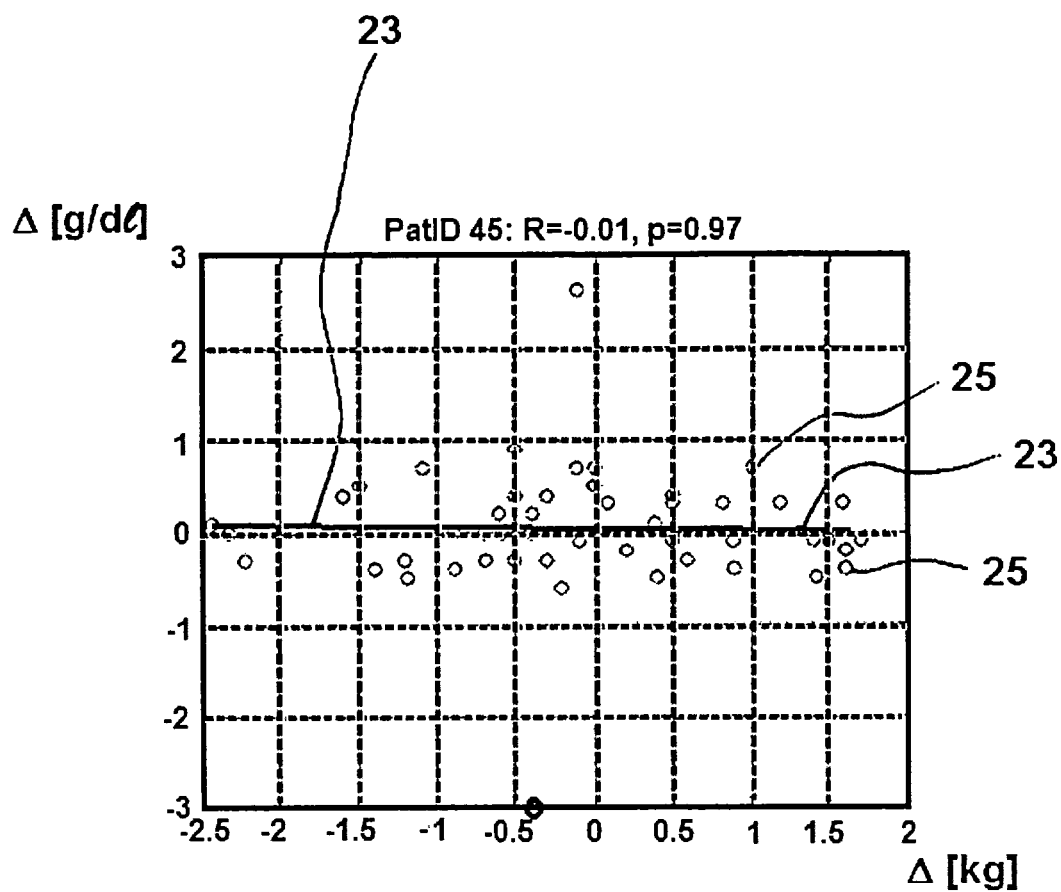
FIG. 4 shows data of another patient in an illustration like that of FIG. 2.

FIG. 4 shows data of another patient in an illustration like that of FIG. 2. However, in contrast to the data shown in FIG. 2, changes in pre-weight are not reflected also in changes of the hemoglobin. Hence, because the hemoglobin concentration remains unchanged it appears that any additional fluid (e.g., water) is stored in the interstitial space, not however at least in parts also in the blood compartment. Hb seems not to be (further) diluted by the additional fluid. The patient which data are shown in FIG. 4 is assumed to be in the saturation range 17 of the Guyton curve as shown in FIG. 1.

Using the Guyton curve—as shown in FIG. 1 or adapted according to one's need—for roughly assessing the patient's Hb sensitivity to amendments to the patient's hydration state can provide additional information about how strongly the patient will react to fluid removal with regard to the patient's Hb concentration. Expressed in different words this may answer the question how strongly the patient may benefit from administering drugs such as EPO (erythropoietin) which effect the hematopoiesis or from enhancing the patient's drug (such as, e.g., EPO) dosage.

More particular, the patient may benefit from first determining the sensitivity of Hb to fluid intake using the delta-Hb over delta-pre-weight plot of FIG. 2 or 4, and—if no significant correlation can be observed as in FIG. 4—first to normalize hydration and only to start EPO (or other anemia affecting or influencing drugs) management when the patient starts becoming more sensitive to water intake in that he has left the saturation range (see, e.g., the range 17 of FIG. 1).

It is to be noted that the above discussion is mainly directed to the case that any increase in weight can be completely attributed to the intake of water (or fluid in general) in distribution volumes where no accumulation of fluid would occur under healthy conditions. In a more general approach it has to be considered carefully which other factors influence the weight and the fluid balance, thus leading to a correction of the relation shown in FIG. 1 so that these influences can be corrected before any conclusions on the distribution of the fluid according to the regions such as 13, 15 or 17 are drawn.

Generally, the impact of food on weight changes may be calculated or estimated by means of the following equation:

$$\text{delta\_}BV = K\_\text{Guyton} * U * \text{delta\_pre-weight} \tag{1}$$

with

U: hydration factor of the ingested food, or by means of ingested food enhanced hydration (depends on the renal function, loss of fluid due to perspiration, diarrhea, vomiting, air humidity, etc.; U can be corrected if the renal function is known, in particular in cases of reduced kidney effectivity), K_Guyton: slope of the Guyton curve, see, e.g., FIG. 1 (ratio: BV over ECW)

delta_BV: difference the in blood volume between two measurements delta_pre-weight: difference in pre-weight between two measurements

EXAMPLE 1

With U=0.7 and K_Guyton=1:3

If a patient's weight increases by 1.0 kg, the blood volume increases by 0.23 L.

It is to be noted that both U and K_Guyton are individual values (K_Guyton even more than U). The water content of food may be approximately constant if a normal diet is followed. That is, U does not change over time as much as K_Guyton. K_Guyton starts to change remarkably when a saturation range is near or reached, see range 17 in FIG. 1. Typically, in the saturation range, K_Guyton is 0, whereas in the linear range 13 illustrated between 0 and 20 L ECW in FIG. 1, K_Guyton is around 1:3.

Typically, U takes values between 0.5 for solid food and 0.8 for more liquid nourishment.

The hydration factor U can be directly determined from the negative slope of curve 23 of FIG. 3. This is particularly possible if the status of the patient is in the linear range 13 of curve 1 or 3 as shown in FIG. 1. For patient whose status is not in the linear range of curve 1 or 3, the following procedure may be advantageously applied: The unknown hydration factor can be determined in advance by means of values obtained from patients who definitely are in the linear range, and the result of this determination can be used as the hydration factor U (or as an approximation thereof) for the patients in question.

Figure 5:
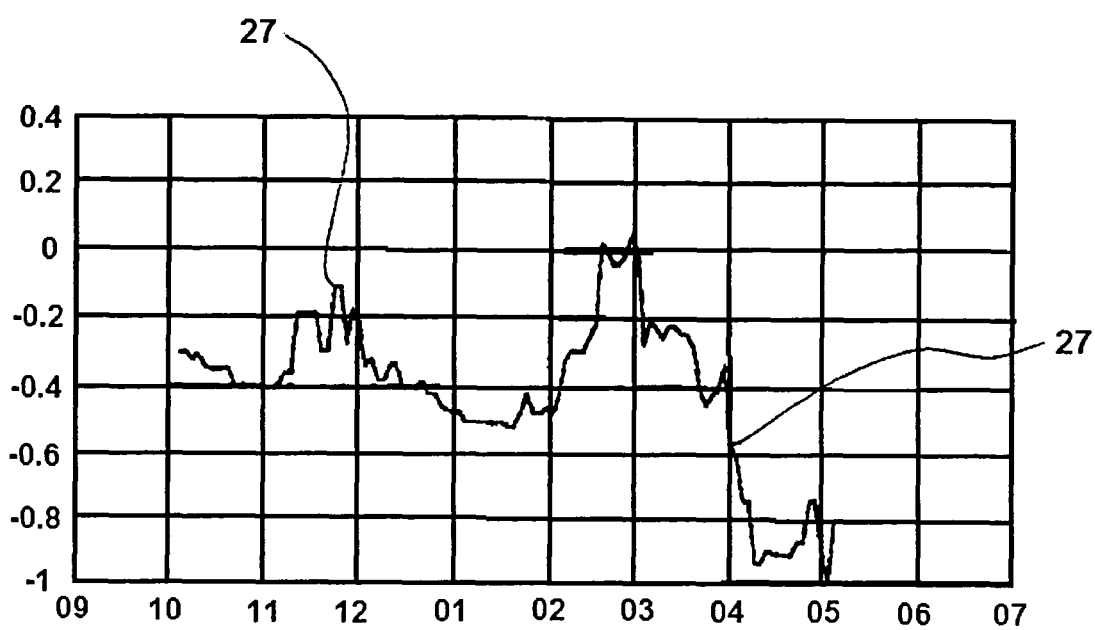
FIG. 5 shows sliding slopes from the representation of FIG. 4 over the year.

FIG. 5 shows another curve 27 illustrating the development of slopes from the representation of FIG. 4 over the year (indicated by months 09 for September, 10 for October, 11 for November and so on), wherein the (absolute) slopes of FIG. 2 were continuously (that is, from one treatment to the next treatment) calculated by means of a sliding window covering four weeks. The calculated slope comes to lie within the middle of the window. For example, in March ("03"), the slope was around 0. That means, the patient was remarkably overhydrated in March. In other words, the patient was deemed to be in the saturation range of the Guyton curve (see range 17 in the illustration of FIG. 1).

It is to be noted that the sliding slopes illustration as shown in FIG. 5 can also be used for illustrating the values shown in FIG. 3.

The sliding window used may cover around 50 days or 20 treatments or any other suitable number of days or treatments or range in general.

Figure 6:
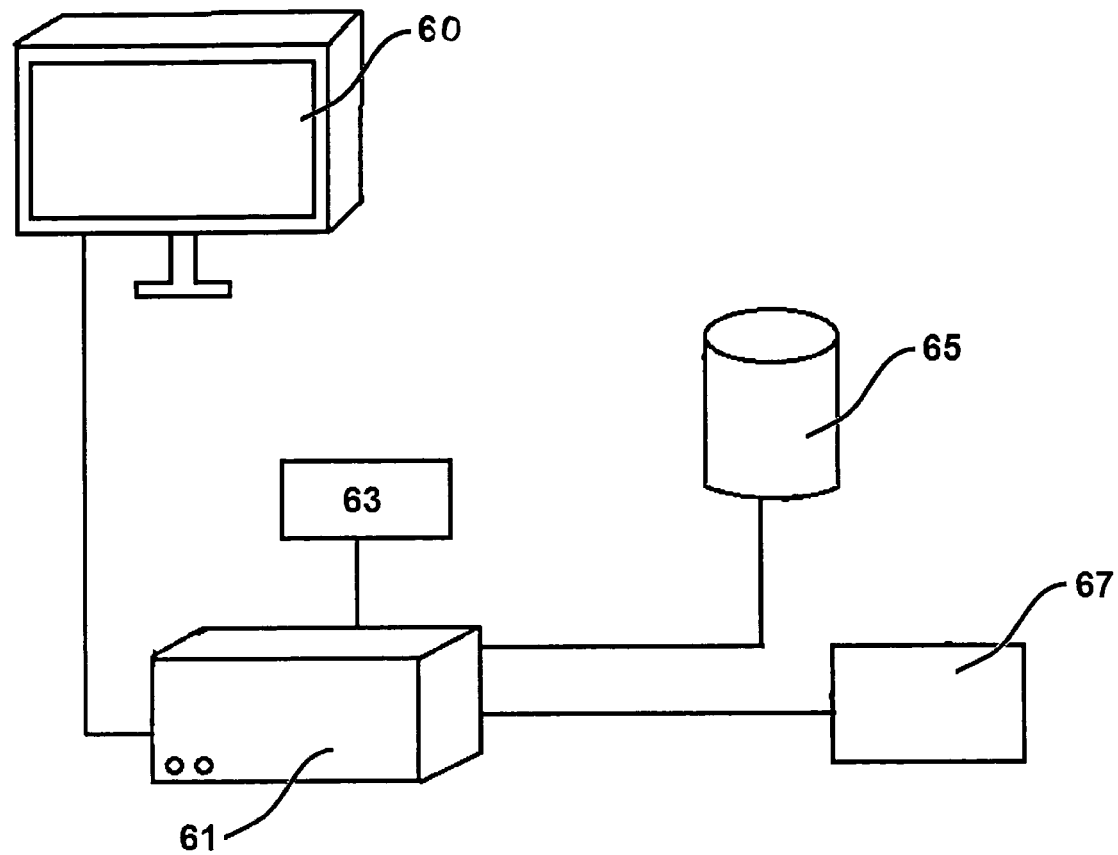
FIG. 6 shows a first apparatus comprising a controller for carrying out the method according to the present invention.

FIG. 6 shows an apparatus 61 comprising a controller 63 configured to carry out the method according to the present invention. The apparatus 61 is connected to an external database 65 comprising the results of measurements and the data needed for the method according to the present invention. The database 65 can also be an internal means of the apparatus 61. The apparatus 61 may optionally have means 67 for inputting data into the controller 63 or into the apparatus 61 itself. Such data may be information about the size of one or more distribution spaces, the mass, the volume, the concentration of a substance as is set forth above, etc., or approximations thereof. Also, the criterion may be input by means of the input means 67. The criterion may, however, alternatively be stored in database 65 or any other storage. The criterion may be calculated or determined by the controller 63 or any other item comprised by the apparatus 61 or interconnected to it. The results of the evaluation, calculation, comparison, assessment etc. performed by the controller 63 and/or the apparatus 61 can be displayed on a monitor 60 or plotted by means of a—not displayed but optionally also encompassed—plotter or stored by means of the database 65 or any other storage means. The database 65 can also comprise a computer program initiating the method according to the present invention when executed.

In particular, the controller 63 can be configured for determining a value reflecting the distribution of the fluid, and for assessing whether the relation fulfills at least one criterion.

Figure 7:
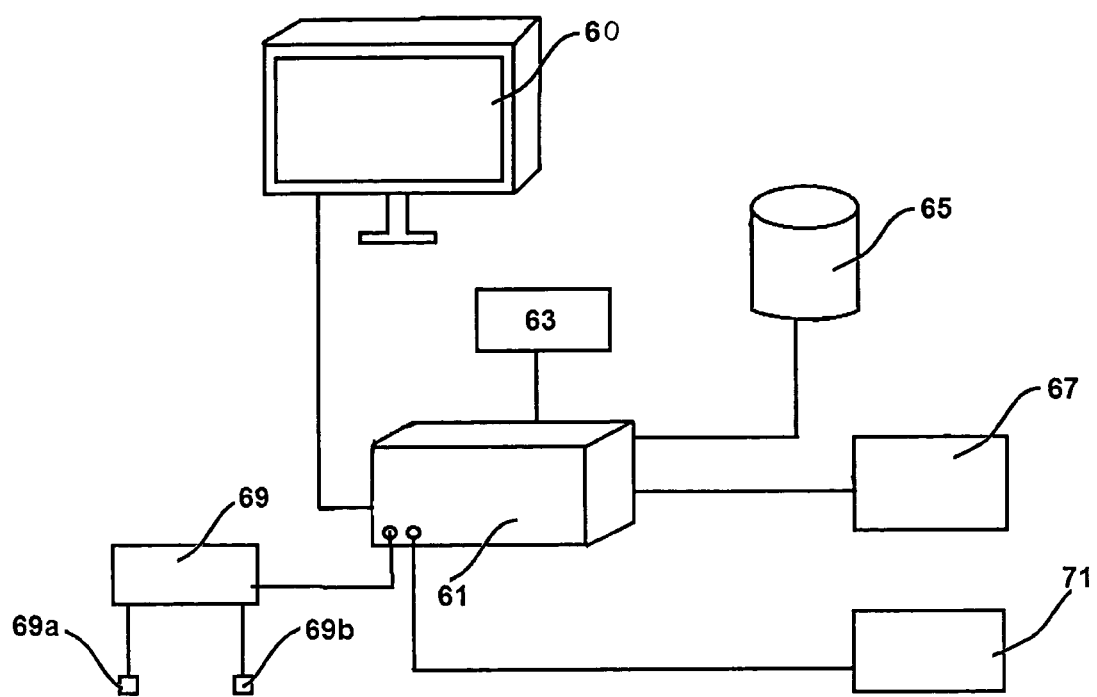
FIG. 7 shows a second apparatus comprising a controller for carrying out the method according to the present invention.

As can be seen from FIG. 7, for corresponding measurements, the apparatus 61 can be connected (by means of wires or wireless) with a bioimpedance measurement means 69 as one example of a means for measuring or calculating the distribution or the size(s) of one or more distribution spaces or approximations or changes thereof. Generally, the means for measuring or calculating can be provided in addition to the external database 65 comprising the results of measurements and the data needed for the method according to the present invention, or in place of the external database 65 (that is, as an substitute).

The bioimpedance measurement means 69 can be capable of automatically compensating for influences on the impedance data like contact resistances.

An example for such a bioimpedance measurement means 69 is a device from Xitron Technologies, distributed under the trademark Hydra™ that is further described in WO 92/19153, the disclosure of which is hereby explicitly incorporated in the present application by reference.

The bioimpedance measurement means 69 may comprise various electrodes. In FIG. 7, only two electrodes 69a and 69b shown which are attached to the bioimpedance measurement means 69. Additional electrodes are, of course, also contemplated.

Each electrode implied can comprise two or more ("sub"-)electrodes in turn. Electrodes can comprise a current injection ("sub"-)electrode and a voltage measurement ("sub"-)electrode. That is, the electrodes 69a and 69b shown in FIG. 12 can comprise two injection electrodes and two voltage measurement electrodes (i.e., four electrodes in total).

Generally spoken, the apparatus according to the present invention can be provided with means such as weighing means, a keyboard, a touch screen etc. for inputting the required data, sensors, interconnections or communication links with a lab, any other input means, etc.

Similarly, the apparatus 61 may have further means 71 for measuring or calculating means for obtaining a value reflecting the distribution of another distribution space and/or for obtaining values reflecting the mass, the volume or the concentration of the substance that can be provided in addition to the external database 65 or in place of the external database 65 (that is, as an substitute).

The means 71 can be provided as a weighing means, a keyboard, touch screen etc. for inputting the required data, sensors, interconnections or communication links with a lab, a Hb (or any other substance suitable for measuring, calculating or approximating the size of a distribution space) concentration probe, any other input means, etc.

Figure 8:
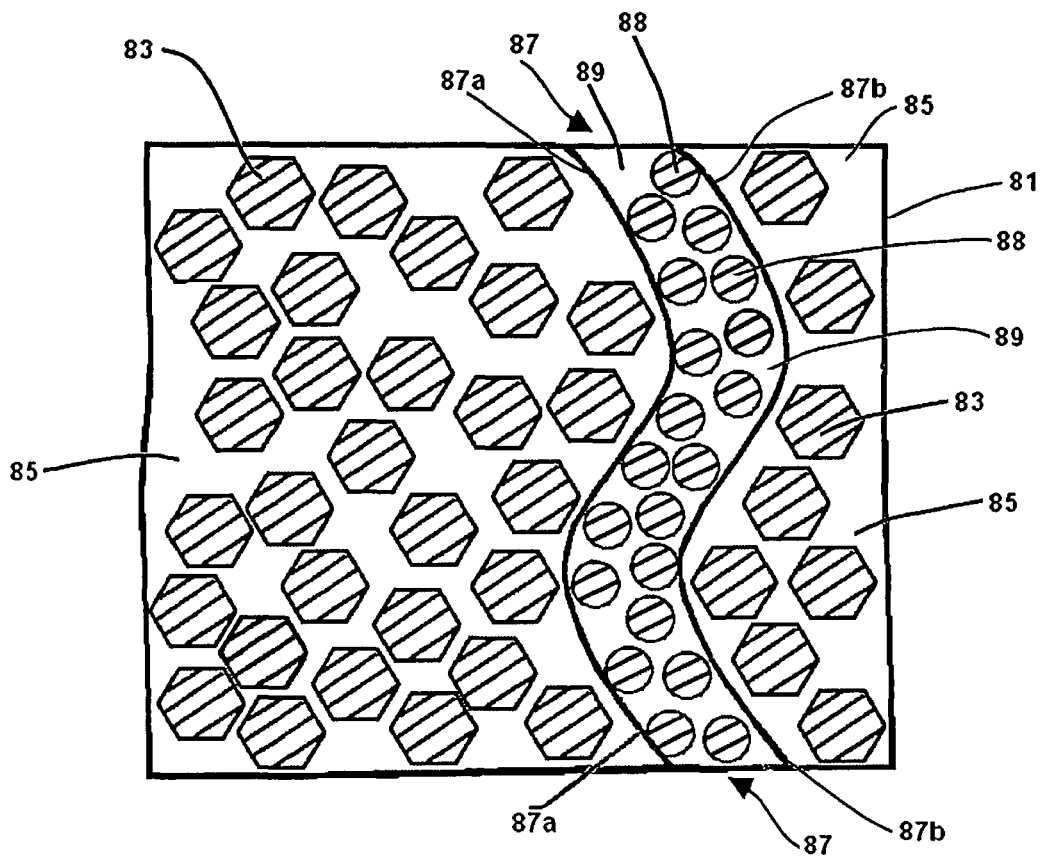
FIG. 8 shows a schematic cut through body tissue for defining certain terms relating to distribution spaces as used within the present specification.

FIG. 8 shows a schematic cut through body tissue for defining certain terms relating to distribution spaces as used within the present specification.

In particular, FIG. 8 shows a defined volume 81 comprising tissue cells 83 comprising intracellular water, an interstitium 85 comprising extracellular water, and a blood vessel 87 with cut vessel walls 87a and 87b.

The blood vessel comprises blood cells 88 (comprising intracellular water). The blood cells are embedded into blood plasma 89 (comprising extracellular water).

Figure 9:
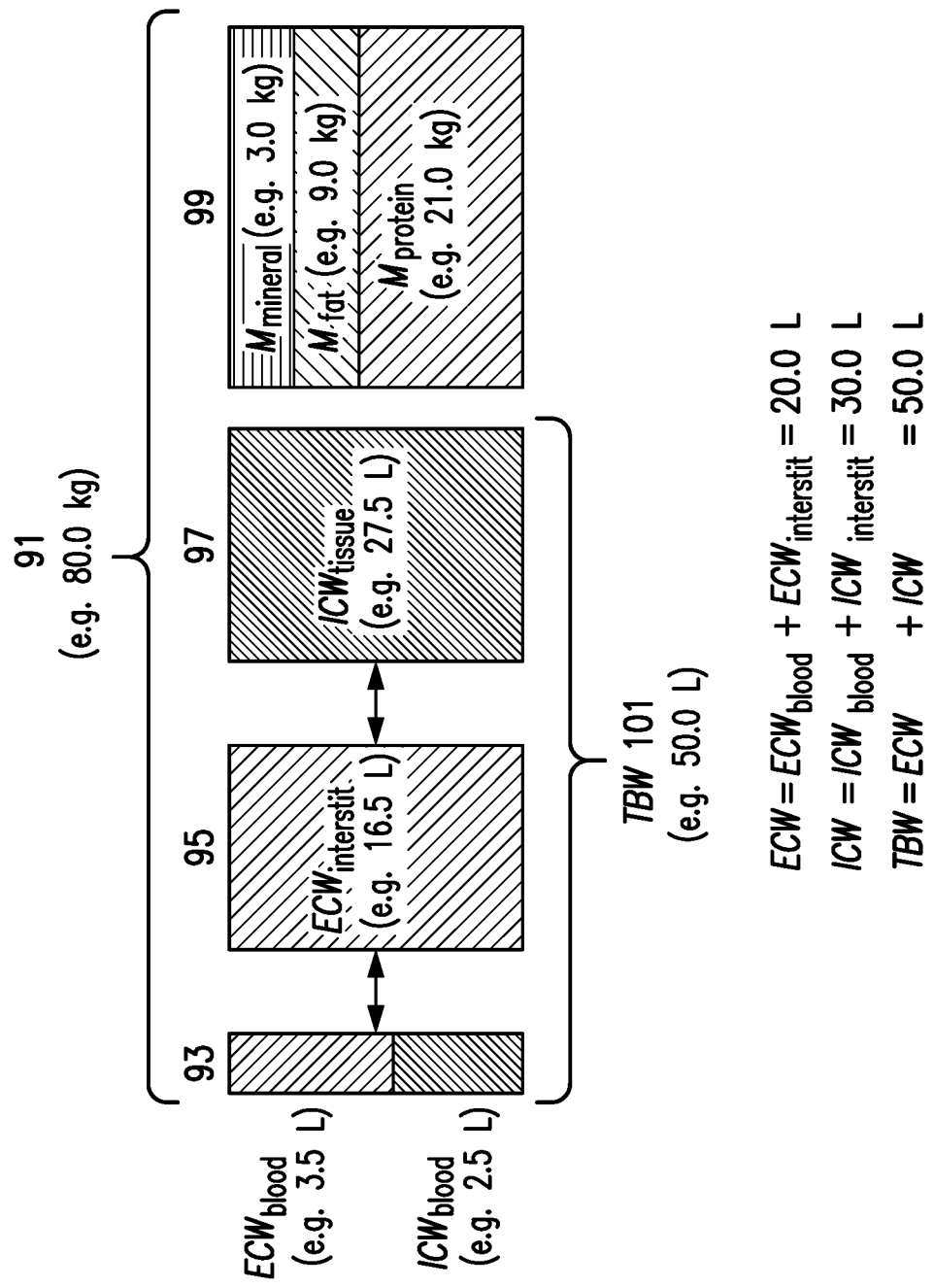
FIG. 9 shows an example of how certain terms relating to distribution spaces may be understood in terms of the present invention and how certain distribution spaces may be interconnected by means of a general concept.

FIG. 9 shows an example of how certain terms relating to distribution spaces may be understood in terms of the present invention. It also shows how certain distribution spaces may be interconnected by means of a general concept.

As can be seen from FIG. 9, the whole body weight 91—which can amount to, for example, 80.0 kg—can be understood as the sum of the blood volume (BV) 93, the water in the interstitium (extracellular) (ECWinterstit) 95, the water in the cells of the tissue (intracellular) (ICWtissue) 97, and the solid components of the body 99.

The blood volume may be understood as the sum of the extracellular water that is present within the vessels (ECWblood), in particular in the blood plasma, and the intracellular water (ICWblood) that is present in the vessel or the (red) blood cells. In an example, the ECWblood may be 3.5 L, the ICW may be 2.5 L, the blood volume 93 may be 6.0 L.

The water in the interstitium (extracellular) 95 (ECWinterstit) can encompass 16.5 L. The water in the cells of the tissue (intracellular) 97 (ICWtissue) can encompass 27.5 L.

The solid components 99 of the body comprise the mineral mass Mmineral which can have 3.0 kg, the fat mass Mfat which can be 9.0 kg, and the protein mass Mprotein which can amount to 21.0 kg. The solid components 99 can thus amount to 33.0 kg.

As can be seen from FIG. 9, the sum of the blood volume 93, the water in the interstitium (extracelluar) 95, and the water in the cells of the tissue (intracellular) 97 can be understood as the total body water 101 (TBW). The total body water 101 can encompass 50.0 L.

As can further be seen from FIG. 9, the sum of the total body water 101 and the solid components 99 can be equal to the whole body weight 91.

As is readily understood by the skilled one, the above given figures and weights are to be understood as examples which may be found in one particular patient, whereas other patients may reveal different weights and mass contributions. However, FIGS. 8 and 9 are well suited for giving one example of how certain terms with regard to distribution spaces may be understood, and also how certain distribution spaces of a patient's body relate to each other.

Again, it is noted that all or at least some of the figures relate to Hb/anemia state and weight/hydration state by means of examples showing how one particular embodiment according to the present invention may be carried out. They are not to be understood as limiting.

The invention claimed is:

1. A blood treatment system for treating blood of a patient, comprising:
   an obtaining system for measuring, at multiple points in time, the patient's: (i) extracellular fluid volume, and (ii) haemoglobin values, the obtaining system configured to:
      determine the patient's blood volume using the haemoglobin values, and
      calculate changes of the extracellular fluid volume and the blood volume over at least two measurements made at different points in time; and
   a control system configured to:
      determine a saturation degree of the patient, wherein the saturation degree is a ratio of the change of the blood volume to the change of the extracellular fluid volume over the at least two measurements made at different points in time,
      assess the patient's sensitivity to fluid addition or fluid removal based on the determined saturation degree and at least one predetermined criterion, and
      adjust treatment parameters of the blood treatment system during a blood treatment based on the assessed patient's sensitivity to fluid addition or fluid removal.

2. The blood treatment system according to claim 1, wherein the blood treatment system is configured to treat a patient by dialysis.

3. The blood treatment system according to claim 2, wherein the blood treatment system is configured to treat a patient or the patient's extracorporeally flowing blood by hemofiltration, ultrafiltration, and/or hemodialysis.

4. The blood treatment system according to claim 1, wherein the blood treatment system further comprises a determining system, said determining system being configured to determine said at least one predetermined criterion.

5. The blood treatment system according to claim 1, wherein the control system is configured to calculate a correlation between relative or absolute values reflecting changes in weight and relative or absolute values reflecting the anemia state of the patient.

6. The blood treatment system according to claim 1, wherein the at least one predetermined criterion is or comprises at least one threshold and/or at least one range.

7. The blood treatment system according to claim 1, wherein said control system is configured to determine said saturation degree based on measurement results obtained from blood samples, urine samples, and/or tissue samples.

8. The blood treatment system according to claim 1, wherein said control system is configured to determine said saturation degree based on results obtained from measuring a concentration, mass, volume or changes thereof of a substance selected from the group consisting of: hemoglobin, albumin, insulin, glucose, C-reactive Protein (CRP), and non-endogeneous-effective substances.

9. The blood treatment system according to claim 1, wherein the control system is configured to assess pre-dialysis or post-dialysis values or calculations of the patient.

10. The blood treatment system according to claim 9, wherein the blood treatment system further includes a plotter for plotting results of the assessment for visual assessment.

11. The blood treatment system according to claim 1, wherein the control system is configured to calculate and/or measure parameters reflecting a volume of at least one of a distribution space of the patient or an approximation thereof.

12. The blood treatment system according to claim 1, wherein the control system is configured to determine or adjust a dosage of a medicament to be administered to the patient during the blood treatment for improving an anemia state of the patient based on the determined saturation degree and the at least one predetermined criterion.

13. The blood treatment system according to claim 1, wherein the obtaining system is or comprises a blood volume measurement device.

14. The blood treatment system according to claim 1, wherein the obtaining system is or comprises a bioimpedance measurement device.

15. The blood treatment system according to claim 1, wherein the blood treatment system further comprises an output device for outputting results provided by the control system.

16. A method for treating blood with a blood treatment system having an obtaining system and a control system, the blood treatment system being configured to assess a patient's fluid status and/or sensitivity to fluid removal from his vascular system or fluid replacement or addition with regard to the patient's hydration state, the method comprising the steps of:

obtaining, by the obtaining system at multiple points in time: (i) values representing an extracellular fluid volume of the patient, and (ii) haemoglobin values of the patient;

determining the patient's blood volume using the haemoglobin values;

calculating changes of the extracellular fluid volume and the blood volume over at least two measurements made at different points in time;

determining a saturation degree of the patient, wherein the saturation degree is a ratio of the change of the blood volume to the change of the extracellular fluid volume over the at least two measurements made at different points in time;

assessing, by the control system, the patient's sensitivity to fluid addition or fluid removal based on the determined saturation degree and at least one predetermined criterion; and adjusting treatment parameters of the blood treatment system during a blood treatment based on the assessed patient's sensitivity to fluid addition or fluid removal.

17. A non-transitory computer-readable medium with an executable program stored thereon, wherein the program instructs a programmable computer system to execute the method according to claim 16.

\* \* \* \* \*

UNITED STATES PATENT AND TRADEMARK OFFICE
CERTIFICATE OF CORRECTION

PATENT NO. : 10,737,009 B2
APPLICATION NO. : 15/179499
DATED : August 11, 2020
INVENTOR(S) : Paul Chamney et al.

Page 1 of 1

It is certified that error appears in the above-identified patent and that said Letters Patent is hereby corrected as shown below:

In the Specification

Column 1, Line 13 (Approx.), Delete "Apr. 20, 2012," and insert -- May 30, 2012, --, therefor;

In the Claims

Column 12, Line 48, Claim 8, Delete "endogeneous" and insert -- endogenous --, therefor.

Signed and Sealed this
Twentieth Day of October, 2020

Andrei Iancu
*Director of the United States Patent and Trademark Office*